US007112903B1

(12) United States Patent
Schob (10) Patent No.: US 7,112,903 B1
(45) Date of Patent: Sep. 26, 2006

(54) MAGNETICALLY JOURNALLED ROTATIONAL ARRANGEMENT INCLUDING A ROTOR FOR GENERATING A UNIPOLAR BIAS MAGNETIC FLUX

(75) Inventor: Reto Schob, Volketswil (CH)

(73) Assignee: Levitronix LLC, Waltham, MA (US)

( * ) Notice: Subject to any disclaimer, the term of this patent is extended or adjusted under 35 U.S.C. 154(b) by 404 days.

(21) Appl. No.: 09/127,644

(22) Filed: Jul. 31, 1998

(30) Foreign Application Priority Data

Aug. 25, 1997 (EP) .................................. 97810596

(51) Int. Cl.
*H02K 7/09* (2006.01)
(52) U.S. Cl. ........................................ 310/90.5
(58) Field of Classification Search .............. 310/90.5, 310/103, 104, 254, 216; 74/5.6 D, 5.6 E, 74/5.46, 5.7, 5.8; 417/423.1, 356, 423.12; 623/3
See application file for complete search history.

(56) References Cited

U.S. PATENT DOCUMENTS

| 4,043,614 | A | * | 8/1977 | Lyman ....................... 310/90.5 |
| 4,077,678 | A | * | 3/1978 | Struder et al. ............. 310/90.5 |
| 4,381,875 | A | | 5/1983 | Studer ........................ 310/90.5 |
| 4,668,885 | A | * | 5/1987 | Scheller ...................... 310/90.5 |
| 6,023,116 | A | * | 2/2000 | Kikuchi et al. ............. 310/90.5 |
| 6,100,618 | A | * | 8/2000 | Schoeb et al. ............. 310/90.5 |
| 6,181,040 | B1 | * | 1/2001 | Schob ......................... 310/90.5 |
| 6,222,290 | B1 | * | 4/2001 | Schob et al. ................ 310/68 B |
| 6,249,067 | B1 | * | 6/2001 | Schob et al. ............... 310/68 B |
| 6,297,574 | B1 | * | 10/2001 | Schob et al. ................ 310/90.5 |
| 6,351,048 | B1 | * | 2/2002 | Schob et al. ................ 310/90.5 |
| 6,355,998 | B1 | * | 3/2002 | Schob et al. ............... 310/68 B |
| 6,365,996 | B1 | * | 4/2002 | Schob ........................ 310/90.5 |
| 6,559,567 | B1 | * | 5/2003 | Schob ........................ 310/90.5 |

FOREIGN PATENT DOCUMENTS

| DE | 945183 | * | 6/1956 | ................ 310/104 |
| DE | 4104250 A1 | | 8/1992 | |
| EP | 0130541 A1 | | 1/1985 | |
| EP | 0177274 | | 4/1986 | |
| EP | 0512516 A1 | | 11/1992 | |
| JP | 59-113316 | * | 6/1984 | ................ 310/90.5 |
| WO | WO 96/31934 | | 10/1996 | |
| WO | WO 97/15978 | | 5/1997 | |

OTHER PUBLICATIONS

Translation of German Reference 945,183, Inventor: Anton Kaspar, published Jul. 1956.*
Translation of WIPO 96/31934, Inventor: Schob et al., published Oct. 1996.*
Translation of Japanese Reference 59-113316, Inventor: Machino, published Jun. 1984.*

* cited by examiner

*Primary Examiner*—Karl Tamai
(74) *Attorney, Agent, or Firm*—Townsend and Townsend and Crew LLP (57) ABSTRACT

A magnetically journalled rotational arrangement includes a substantially disc-shaped or ring-shaped rotor and a stator. The stator includes structure for the production of a field which produces a rotation of the rotor. The rotor has structure which produce a unipolar bias magnetization flux which is spatially modulated when viewed in the circumferential direction.

15 Claims, 10 Drawing Sheets

MAGNETICALLY JOURNALLED ROTATIONAL ARRANGEMENT INCLUDING A ROTOR FOR GENERATING A UNIPOLAR BIAS MAGNETIC FLUX

BACKGROUND OF THE INVENTION

1. Field of the Invention

The invention relates to a magnetically journalled rotational arrangement including a substantially disc-shaped or ring-shaped magnetically journalled rotor and stator.

2. Description of the Prior Art

Magnetically journalled rotational arrangements are used today in numerous fields of application, in particular, where mechanically journalled rotational arrangements have considerable disadvantages, thus e.g., in stirrers or forwarding apparatuses for highly pure or biological liquids such as, for example, blood. Magnetically journalled rotational arrangements are also useful in applications such as clean room blowers or carrier apparatuses for wafers (so-called wafer carriers) where high demands are placed on cleanliness and no contamination, such as is caused e.g., by gases which can escape from the lubricants of mechanical bearings, may be tolerated. In these applications, both the journalling of the rotor (which can be designed, e.g., as the vaned wheel of a pump) and a rotational movement of the same must be possible.

A magnetically journalled rotational arrangement with a flywheel is described in EP-A-0,130,541. Apparatuses of this kind are used, for example, in the control of the orientation of satellites. Ring-shaped permanent magnets for the magnetic journalling of the rotor are provided both in the rotor and in the stator; moreover the stator also comprises control windings in order to be able to correct possible deflections of the rotor from the desired position. Further separate drive means for driving the rotor are also provided in the rotor and in the stator. This has the result that the total construction is relatively complicated and expensive.

SUMMARY OF THE INVENTION

The object of the present invention is to provide a magnetically journalled rotational arrangement by means of which a magnetic journalling as well as a rotation of the rotor can be produced at the same time. The magnetically journalled rotational arrangement should be as uncomplicated and inexpensive as possible and should, in particular, also permit the initially named uses.

DETAILED DESCRIPTION OF THE PREFERRED EXEMPLARY EMBODIMENTS

Figure 1A:
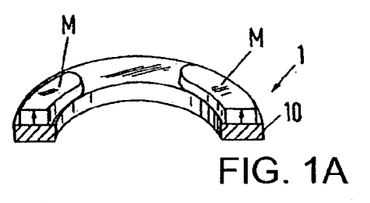
FIG. 1 shows exemplary embodiments of the rotor of the rotational arrangement in accordance with the invention with axially magnetized permanent magnets arranged at one side of the rotor.
Figure 1B:
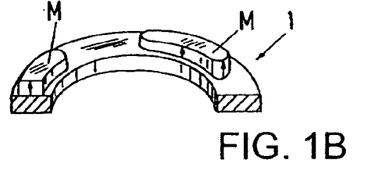
Figure 1C:
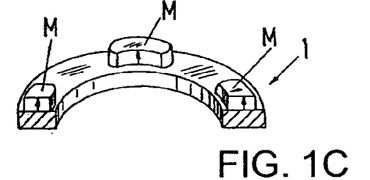

In FIG. 1 one recognizes three exemplary embodiments of a rotor 1 of the rotational arrangement in accordance with the invention. The three rotors 1 each comprise axially magnetized, discrete permanent magnets M arranged at the one side of the rotor—at the upper surface of a ring 10 consisting of a ferromagnetic material. These permanent magnets produce a unipolar (the magnets on this side of the rotor are all magnetized in the same direction) bias magnetization flux which emerges radially from the ring 10. In the region of the ring 10, (between the permanent magnets M) the bias magnetization flux is right homogeneous when viewed in the circumferential direction. In all, it is considerably spatially modulated in the circumferential direction because gaps are continually provided between the individual discrete permanent magnets M. Through the interaction of a corresponding rotary or alternating field with the spatially modulated unipolar bias magnetization flux, a torque is produced in the rotor 1. The three rotors shown in FIG. 1 differ essentially in the number of poles or pole pairs. The rotor at the top has exactly four poles (two pole pairs), whereas the middle rotor has six poles (three pole pairs) and the bottom has eight poles (four pole pairs).

Figure 2A:
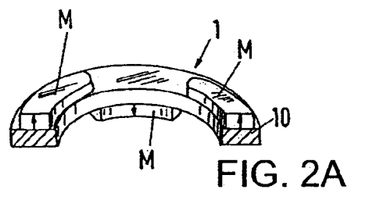
FIG. 2 shows exemplary embodiments of the rotor of the rotational arrangement in accordance with the invention with axially magnetized permanent magnets arranged at both sides of the rotor.
Figure 2B:
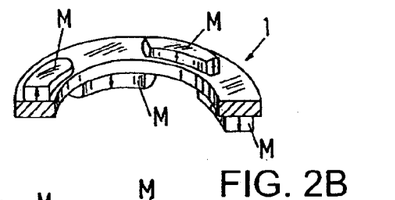
Figure 2C:
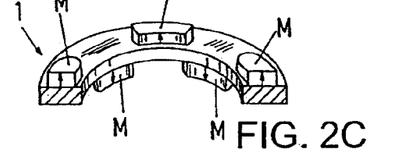

The exemplary embodiments of the rotor 1 shown in FIG. 2 have permanent magnets M which are arranged on both sides of the rotor (that is, at the upper and the lower surface of the rotor) with the direction of magnetization of the permanent magnets M at the upper surface of the rotor being opposite to the direction of magnetization of the permanent magnets M at the lower surface of the rotor (both at the upper and the lower surface always having the same direction, that is, being unipolar).

Figure 3A:
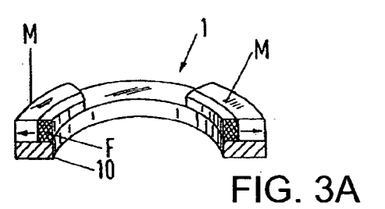
FIG. 3 shows exemplary embodiments of the rotor of the rotational arrangement in accordance with the invention with radially magnetized permanent magnets arranged at one side of the rotor.
Figure 3B:
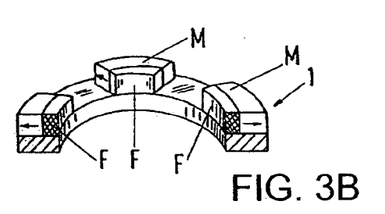
Figure 4A:
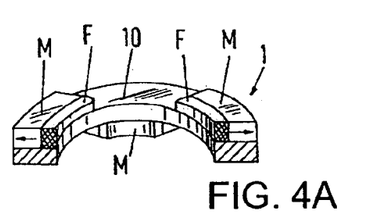
FIG. 4 shows exemplary embodiments of the rotor of the rotational arrangement in accordance with the invention with radially magnetized permanent magnets arranged at both sides of the rotor.
Figure 4B:
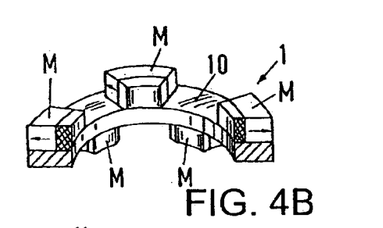

FIG. 3 shows exemplary embodiments of the rotor 1 in which permanent magnets M are arranged at one side of the rotor only, whereas permanent magnets are arranged at both sides of the rotor in the exemplary embodiments of the rotor in accordance with FIG. 4. Contrary to the exemplary embodiments of FIG. 1 and FIG. 2, the permanent magnets M are radially magnetized. Furthermore, additional ferromagnetic elements F (e.g., of iron) are provided for a better conduction of the magnetic flux.

Figure 5:
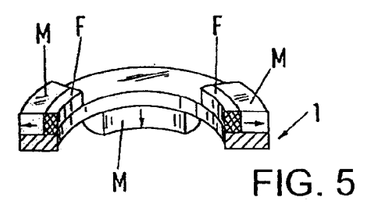
FIG. 5 shows an exemplary embodiment of the rotor with permanent magnets which are arranged on both sides of the rotor and are axially magnetized on the one side of the rotor and radially magnetized at the other side.
Figure 6:
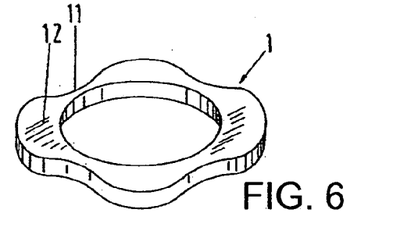
FIG. 6 shows an exemplary embodiment of the rotor with projections and recesses between these projections (reluctance rotor)
Figure 7A:
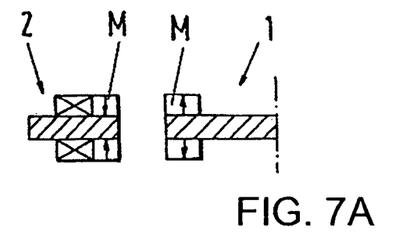
FIG. 7 shows exemplary embodiments of possible arrangements of the permanent magnets.
Figure 7B:
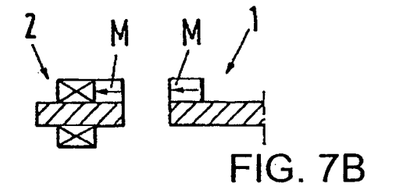
Figure 7C:
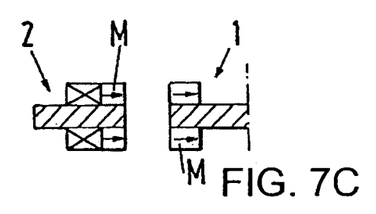
Figure 7D:
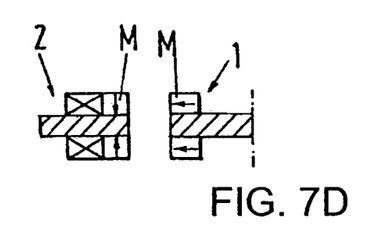
Figure 7E:
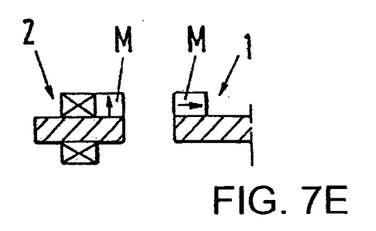
Figure 7F:
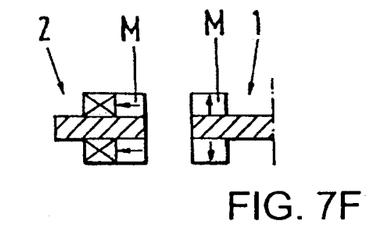
Figure 7G:
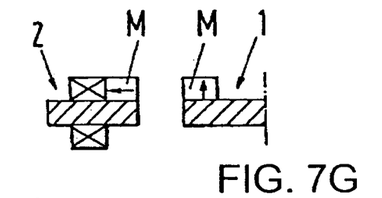
Figure 7H:
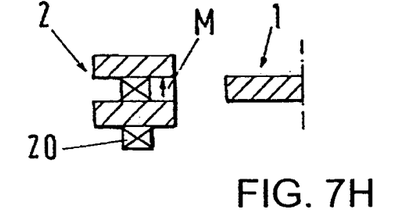
Figure 7I:
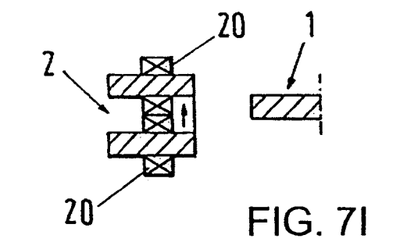
Figure 7J:
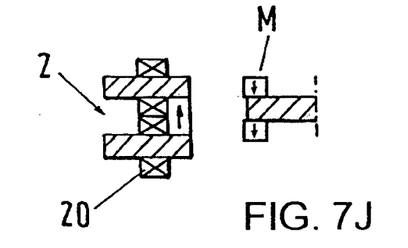

FIG. 5 shows an exemplary embodiment of the rotor 1 in which permanent magnets M are arranged at both sides of the rotor; on the one (here: the lower) side of the rotor, axially magnetized permanent magnets; on the other (here: the upper) side of the rotor, radially magnetized permanent magnets. FIG. 6 shows an exemplary embodiment of the rotor with projections 12 and recesses 11 in which the modulation of the unipolar bias magnetization flux is thus produced by soft magnetic anisotropy. This type of rotor is also known as a reluctance rotor.

In FIG. 7, a plurality of embodiments of possible arrangements of the permanent magnets are illustrated. There one recognizes, beginning in the left column from top to bottom and then in the right column from top to bottom:

axially magnetized permanent magnets M on both sides of the rotor 1 as well as in the stator 2 radially magnetized permanent magnets M on one side of the rotor 1 as well as in the stator 2 radially magnetized permanent magnets M on both sides of the rotor 1 as well as in the stator 2 radially magnetized permanent magnets M on both sides of the rotor 1 and axially magnetized permanent magnets M on both sides in the stator 2 radially magnetized permanent magnets M on one side of the rotor 1 and axially magnetized permanent magnets M on one side in the stator 2 axially magnetized permanent magnets M on both sides of the rotor 1 and radially magnetized permanent magnets M on both sides in the stator 2 axially magnetized permanent magnets M on one side of the rotor 1 and radially magnetized permanent magnets M on one side in the stator 2 axially magnetized permanent magnets M in the stator 2 and no permanent magnets on the rotor 1 (reluctance rotor), only one control winding 20 in the stator 2 axially magnetized permanent magnets M in the stator 2 and no permanent magnets on the rotor 1 (reluctance rotor), two control windings 20 in the stator 2 axially magnetized permanent magnets M in the stator 2 and in the rotor 1, two control windings in the stator 2. The magnetizations shown here can, in principle, also be oriented in reverse.

Figure 8:
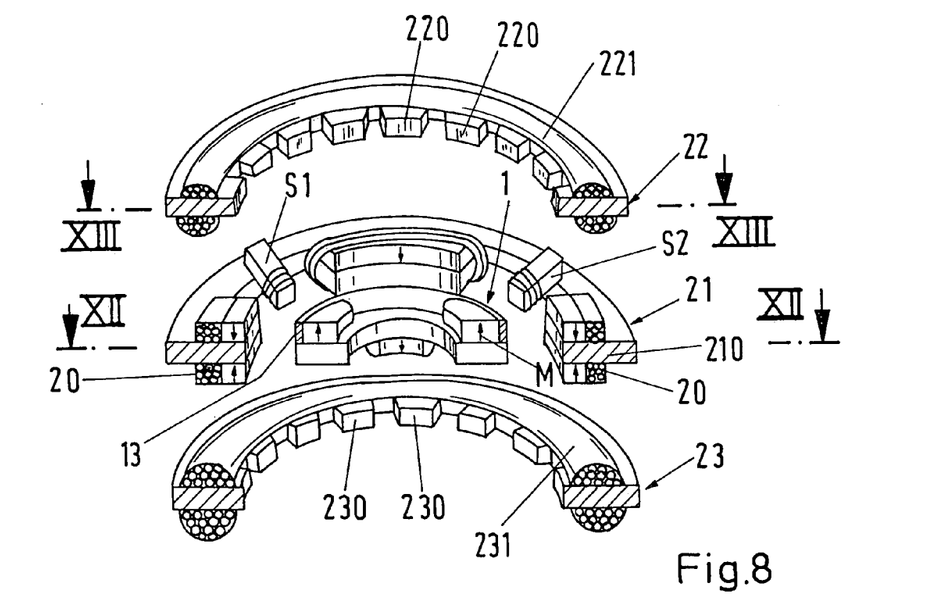
FIG. 8 shows an exemplary embodiment of a rotational arrangement in accordance with the invention with a bearing stator and two motor stators in an exploded view.

In FIG. 8, an exemplary embodiment of a rotational arrangement in accordance with the invention can be recognized in an exploded view. In this exemplary embodiment, the stator also comprises, in addition to a ring-shaped bearing stator 21 which produces the magnetic journalling of the rotor 1 in the bearing plane, two further motor stators 22 and 23, of which the one motor stator 22 is arranged in a first motor plane parallel to the bearing plane on the one (here: the upper) side of the bearing stator 21 and the other motor stator 23 is arranged in a second motor plane parallel to the bearing plane on the other (here: the lower) side of the bearing stator 21.

If one observes the bearing plane, one recognizes that the rotor 1 has axially magnetized permanent magnets M which are arranged on both sides of the rotor. Furthermore, a sensor ring 13 of a magnetically poorly conducting material, which is, however, of good electrical conductivity (e.g., aluminum), in which eddy currents arise during operation, which in turn produce magnetic fields which can be evaluated with the help of sensors S1, S2 in the bearing stator 21, is provided at the rotor 1. In this manner, (which is known per se), the position of the rotor 1 can be precisely determined and, where required, corrected at any point in time.

The ring-shaped bearing stator 21 has teeth 210 which point in the radial direction toward the rotor 1 and on which, on the one hand, the stator-side permanent magnets M and, on the other hand, the control windings 20 are arranged. With the help of the control windings the permanent magnet flux can be selectively reinforced or weakened so that when a deviation of the rotor 1 away from the desired position of the rotor 1 arises, the rotor 1 can be moved back to the desired position again.

The two ring-shaped motor stators 22 and 23 likewise have teeth 220 and 230 pointing inwardly in the radial direction. Furthermore, they are each provided with a rotary field winding 221 and 231, respectively, by means of which a corresponding rotary field can be produced in order to drive the rotor 1 rotationally. Rotary field windings 221 and 231 of this kind are known per se—they are therefore only schematically illustrated in FIG. 8. Since the number of poles or pole pairs in the rotor and the stator must agree, and since the rotor has a number of poles of four (two pole pairs) on both sides, the rotary field windings must also be designed in such a manner that a four-pole rotary field is produced in the motor stator. Naturally, it is also possible to omit one of the two motor stators, through which the torque is halved. In this case, it is also sensible to omit the permanent magnets on the corresponding side of the rotor. In this manner, the constructional height of the arrangement can be reduced.

Figure 9:
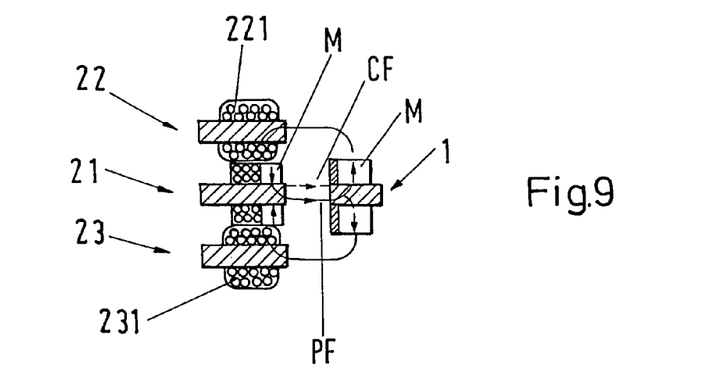
FIG. 9 shows the exemplary embodiment of FIG. 8 in section.

FIG. 9 shows the exemplary embodiment of FIG. 8 in a section. One recognizes in FIG. 9, on the one hand, the distribution of the magnetic flux produced by the permanent magnets M (solid line PF), which goes out from the permanent magnets M to the rotor 1, leads via the air gap into the motor stator 22 or 23, respectively, (consisting of a ferromagnetic material), leads further from there via the permanent magnets M in the bearing stator 21, through the ferromagnetic material (e.g., iron) of the bearing stator 21 and its teeth 210 via the air gap between the bearing stator 21 and the rotor 1 back into the ferromagnetic material (e.g., iron) of the rotor 1, and then finally closes again in the permanent magnets M of the rotor 1. A part of the permanent magnet flux also passes directly from the permanent magnets M on the rotor 1 into the permanent magnets M on the bearing stator 21, which is not illustrated in FIG. 9.

Figure 10:
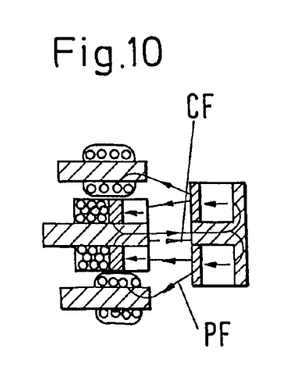
FIG. 10 shows an exemplary embodiment analogous to FIG. 8, in section, with radially magnetized permanent magnets.
Figure 11:
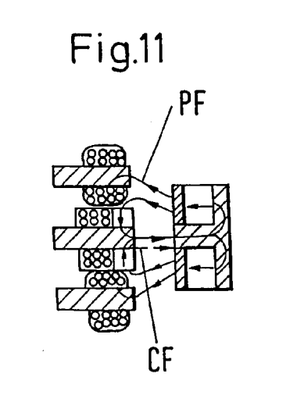
FIG. 11 shows an exemplary embodiment analogous to FIG. 8, in section, with radially magnetized permanent magnets in the rotor and axially magnetized permanent magnets in the stator.

Furthermore, in FIG. 9 one also recognizes in the air gap between the bearing stator 21 and the rotor 1, the control flux (broken line CF) which can be produced with the help of the control windings 20 for the correction of deviations of the rotor from the desired position. The closed magnetic circuit of the control flux is not recognizable in FIG. 9 since it extends in the bearing plane and thus, in principle, in a plane perpendicular to the plane of the permanent magnet flux (for this, see FIG. 12). A reinforcement or a weakening of the permanent magnet flux can be produced only in the region of the teeth 210 and in the air gap between the bearing stator 21 and the rotor 1 (and naturally also at the entry into the rotor), because here the two field components, which otherwise do not influence each other, have the same orientation. FIG. 10 and FIG. 11 each show an arrangement analogous to FIG. 8 in an illustration analogous to FIG. 9. In contrast to FIG. 8 and FIG. 9, the permanent magnets M in the rotor 1 and in the bearing stator 21 in FIG. 10 are both radially magnetized; in FIG. 1 the permanent magnets M in the rotor 1 are radially magnetized whereas they are axially magnetized in the bearing stator 21.

Figure 12:
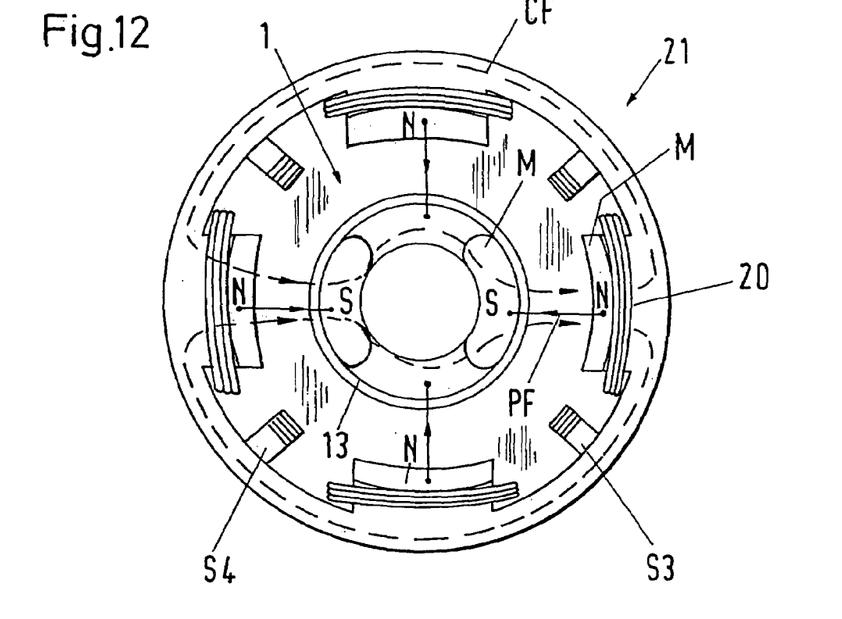
FIG. 12 shows a plan view of the rotor of the exemplary embodiment of FIG. 8.

FIG. 12 shows a plan view of the rotor in accordance with the exemplary embodiment of FIG. 8, that is, a plan view onto the bearing plane. In this illustration, one now better recognizes the distribution of the control flux CF (broken line) which can be produced with the help of the control windings 20 in order to be able to move the rotor 1 back into the desired position in the event of a deviation from its desired position. It is clear that a part of the control flux is also closed back via the two other stator teeth, which is not illustrated here for reasons of greater clarity. Furthermore, the path of the permanent magnet flux PF (solid line) naturally does not show up well in this illustration; for the distribution of the permanent magnet flux see FIG. 9. Finally, in FIG. 12, one also recognizes the two additional sensors S3 and S4, which are not recognizable in the illustration in accordance with FIG. 8.

Figure 13:
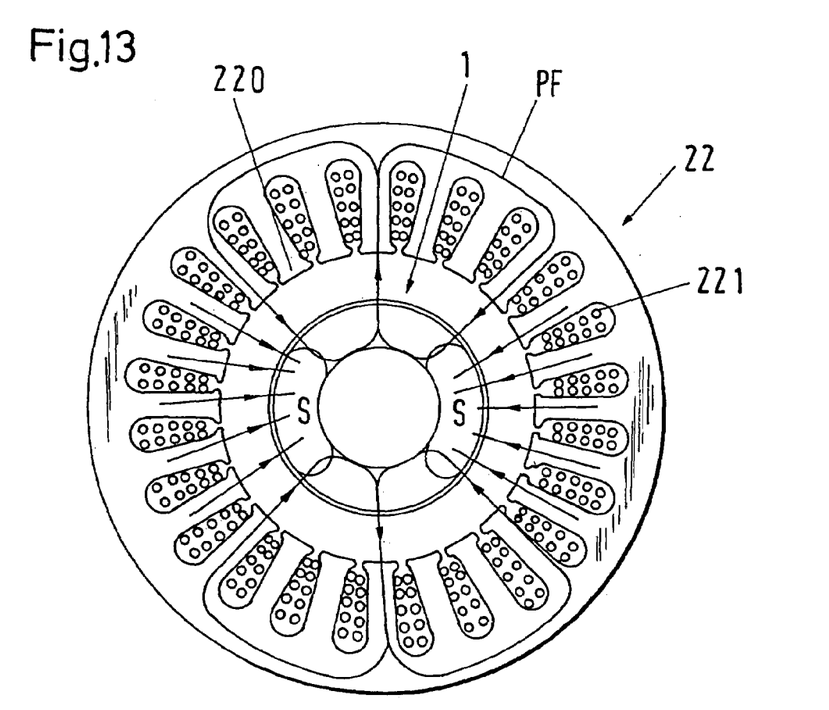
FIG. 13 shows an illustration of a section along the line XIII—XIII in FIG. 8.

FIG. 13 shows a section along the line XIII—XIII in FIG. 8, that is, a section in the first motor plane. One recognizes here the motor stator 22 and the distribution of the permanent magnet flux produced by the permanent magnets M. Furthermore, one also recognizes the—here four poled—rotary field winding 221 which is embedded into the individual grooves of the motor stator 22 (the rotary field itself is not illustrated). How a rotary field of this kind can be executed is sufficiently known to the expert and will therefore not be discussed here in further detail.

Figure 14:
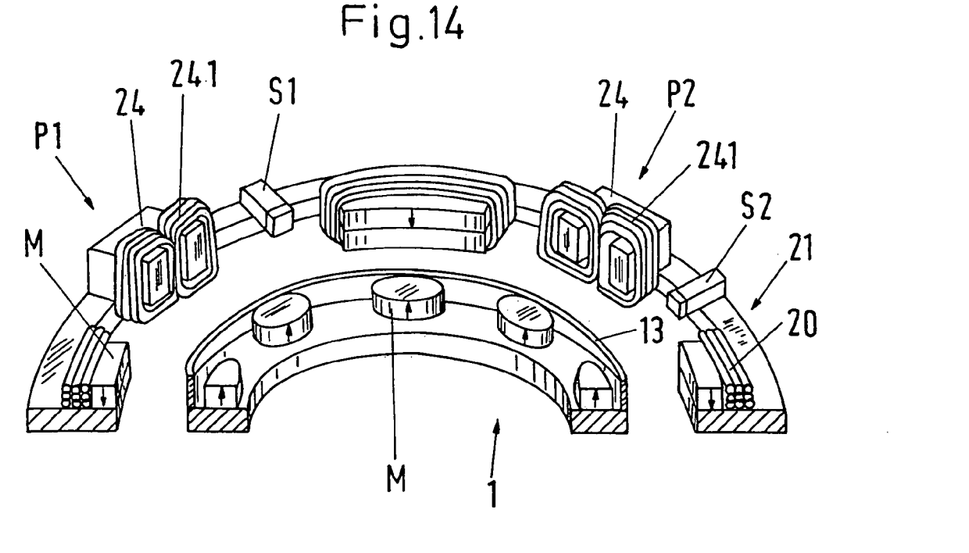
FIG. 14 shows a further embodiment of the rotational arrangement in accordance with the invention (segment arrangement)

FIG. 14 shows a further exemplary embodiment of the rotational arrangement in accordance with the invention, in this case, a segment arrangement. This designation derives from the fact that the means for the production of the rotary field (or the alternating field) are also arranged in the individual segments between the permanent magnets M in the bearing stator 21, namely in the form of U-shaped coil cores 24 (e.g., iron cores) on which windings 241 are wound by means of which a rotary field (or an alternating field) can be produced. The U-shaped coil cores 24 are arranged here in the bearing plane, so to speak. The advantage is a low constructional height. One recognizes that the exemplary embodiment shown in FIG. 14 is a rotor with the pole number sixteen (eight pole pairs). The arrangement illustrated here is a two phase arrangement which in principle can have 2, 4, 6, 8, . . . etc., U-shaped coil cores 24; here it has four coil cores 24, two of which are illustrated (due to the half-section illustration).

Figure 15:
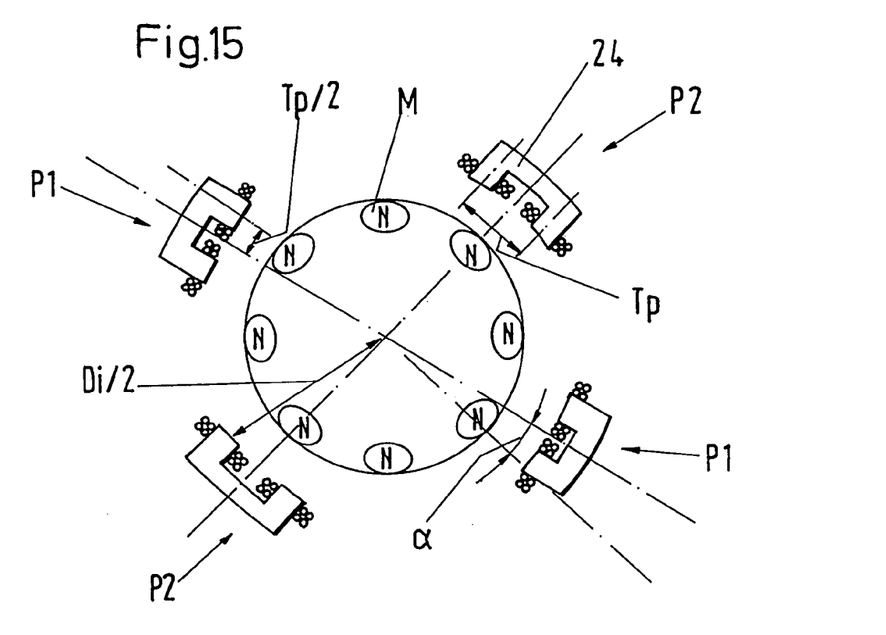
FIG. 15 is an illustration of the principle of the arrangement of the U-cores and of the motor windings wound around them.

In FIG. 15, the arrangement of the U-shaped coil cores 24 and the windings 241 which are wound around these coil cores 24 can be recognized in an illustration of the principle. The windings of mutually oppositely lying coil cores are each flowed through by the same current; they can be connected in series or in parallel. The two phases P1 and P2 (it is a two-phase arrangement) are mutually electrically displaced by 90°. The pole division Tp amounts to:

$$Tp=(\pi \cdot Di)/2p$$

where Di designates the inner diameter of a circle which is tangent to the poles of the U-shaped coil cores 24 near the rotor 1; hence, Di/2 represents the radius of this circle (see FIG. 15), and p the number of pole pairs.

The permanent magnets M on the rotor 1 each follow one another displaced by an angle of 45° (there are eight permanent magnets M which are uniformly distributed over an angle of 360°). If one were now to likewise arrange the four U-shaped coil cores 24 over the angle of 360° with the same regularity (thus displaced with respect to one another by a geometrical angle of 90°), then exactly one permanent magnet M of the rotor each would come to lie between and in front of the U-shaped coil cores at the same time. Completely independently of the electrical displacement angle of the two phases P1 and P2, no starting up of the rotor 1 can take place in this manner since when the magnetic field increases or decreases, the respective permanent magnet on the rotor 1 will only be more or less strongly attracted or repelled by the respective U-shaped coil core 24. One would thus have to supply an impulse (e.g., mechanically) to the rotor at first in order to set it rotating.

In order now that an electrical start-up of the rotor be possible, the two phases P1 and P2 (which are electrically displaced by 90°) must be mutually geometrically displaced, and indeed, ideally in such a manner that one permanent magnet comes to lie completely in front of the coil core of the one phase when another permanent magnet comes to lie exactly half in front of the coil core of the other phase so that a torque acting on the rotor 1 can always be produced with one of the two phases P1 or P2. This geometrical displacement amounts to:

$$(360°/2p) \cdot ((1/m)+k),$$

where p stands for the number of pole pairs (here 8), m designates the number of phases (here 2) and k is a natural number, which amounts here, in principle, to the displacement angle $11.25°+k\ 22.5°$; in particular, in the exemplary embodiment shown, k=4. One recognizes in FIG. 15 the angle α=11.25° and the corresponding displacement of the coil cores 24. Analogously to this example, arrangements with any desired phase numbers, in particular, also one and three phase arrangements as well as any desired numbers of pole pairs, are possible. It is also conceivable to use motor segments with a plurality of grooves per pole division and with an approximately sinusoidal flux distribution. Air gap windings are likewise conceivable in order to prevent groove latch torques where possible.

Figure 16:
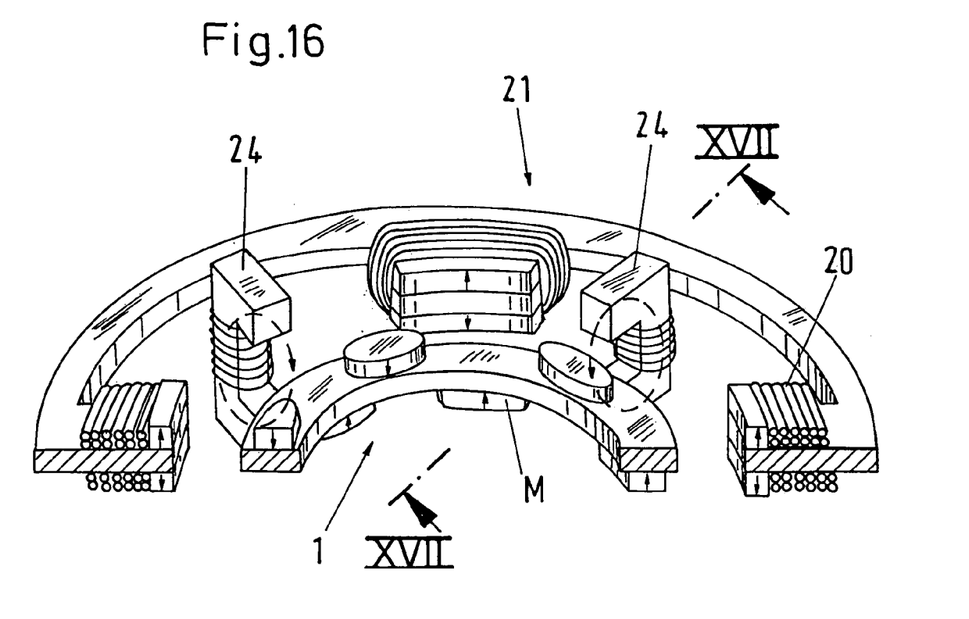
FIG. 16 shows an exemplary embodiment of the rotational arrangement in accordance with the invention analogous to FIG. 14, but with U-cores arranged perpendicular to the bearing plane.
Figure 17:
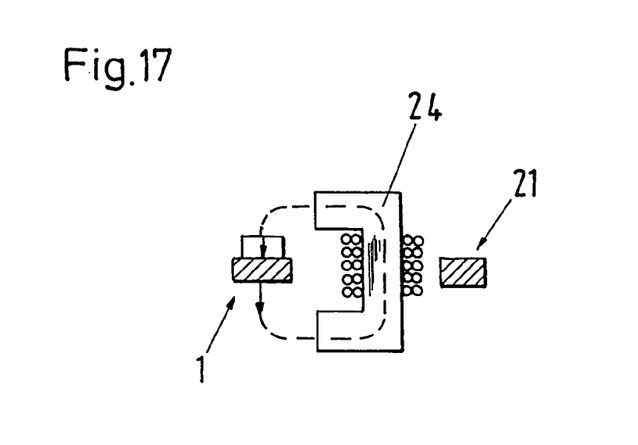
FIG. 17 shows a section along the line XVII—XVII in FIG. 16.

FIG. 16 shows a further exemplary embodiment of the rotational arrangement in accordance with the invention which corresponds to the exemplary embodiment of FIG. 14 as regards the basic principle in which the coil cores 24 are arranged perpendicular to the bearing plane. Moreover, permanent magnets M are also arranged on both sides of the rotor 1; the corresponding is true of the bearing stator 21 as well. FIG. 17 shows a corresponding section along the line XVII—XVII in FIG. 16. An arrangement of this kind corresponds to a "transversal flux motor" shown here as a segment motor with split phase.

Figure 18:
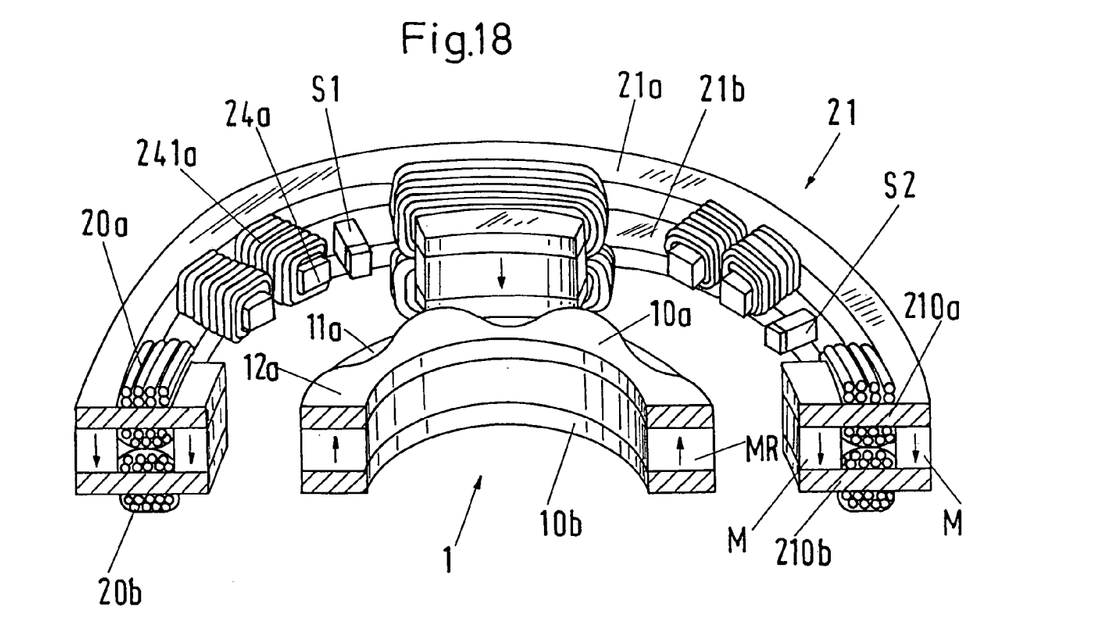
FIG. 18 shows a further exemplary embodiment of the rotational arrangement in accordance with the invention with two ring-shaped iron yoke closures at the rotor, one of which is provided with projections and recesses.

FIG. 18 shows a further exemplary embodiment of the rotational arrangement in accordance with the invention. In this exemplary embodiment, the rotor 1 comprises two rings 10*a* and 10*b* consisting of a ferromagnetic material which has projections 12*a* and recesses 11*a* (or 12*b* and 11*b*, respectively, which are not recognizable) (reluctance rotor). An axially magnetized permanent magnet ring MR, which is not structured, is arranged between the two rings 10*a* and 10*b*. The ring-shaped bearing stator 21 likewise comprises two rings 21*a* and 21*b*, with two axially magnetized permanent magnets M being arranged between the teeth 210*a* and 210*b* of the two rings. Furthermore, one also recognizes the control windings 20*a* and 20*b* (in principle, only one control winding is required) as well as the sensors S1 and S2 for the determination of the respective current position of the rotor. The means for driving the rotor 1 are formed on at the upper ring 21*a* of the bearing stator 21 in the form of coil cores 24*a*, with corresponding windings 241*a* being wound around the coil cores 24*a*. This exemplary embodiment is distinguished by a high permanent magnetic bias magnetization flux, which enables the air gap between the stator and the rotor to be enlarged for certain applications and nevertheless enables a reliable magnetic journalling to be achieved.

Figure 19:
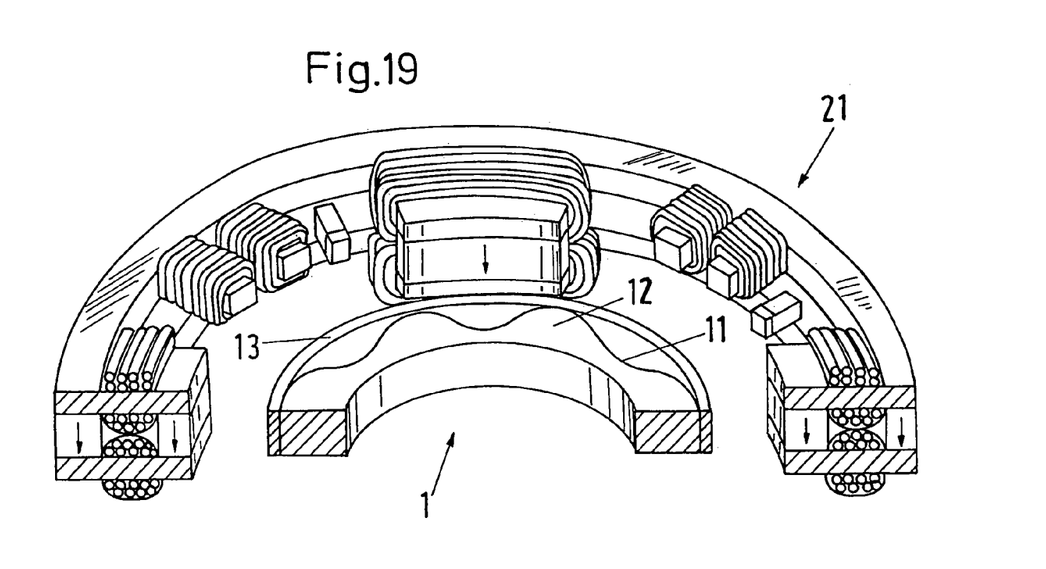
FIG. 19 shows a further exemplary embodiment of the rotational arrangement in accordance with the invention in which the entire rotor has projections and recesses and is surrounded by a magnetically poorly conducting ring.

The exemplary embodiment of FIG. 19 differs from the exemplary embodiment of FIG. 18 substantially through the different embodiment of the rotor 1. The latter comprises no permanent magnets, but is of a ferromagnetic material, has the said structure with the projections 12 and recesses 11 and is surrounded by a sensor ring 13 of a magnetically poorly conducting but electrically well conducting material (e.g., of aluminum). This exemplary embodiment is advantageous, in particular, for applications in which the rotor 1 must be thrown away or recycled after a single use because this is dictated by the corresponding application (e.g., when pumping blood). The rotor 1 is namely comparatively simple and economical to manufacture due to the absence of or, respectively, the presence of non-existent, permanent magnets.

Figure 20:
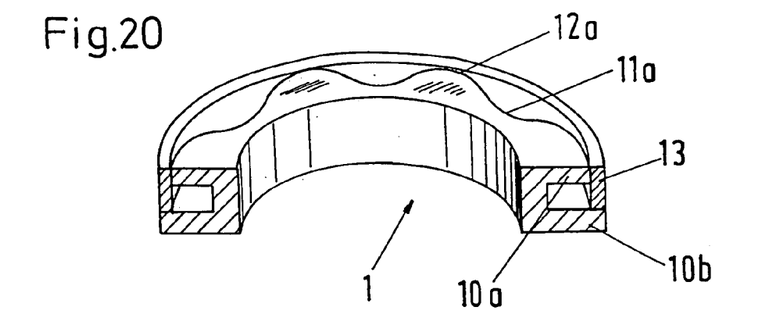
FIG. 20 shows an exemplary embodiment of the rotor in which the rotor has a U-shaped profile, is partially provided with projections and recesses and is partially surrounded by a magnetically poorly conducting ring.

FIG. 20 shows an exemplary embodiment of a rotor 1 which is manufactured of a ferromagnetic material and has a U-shaped profile. It is surrounded by a sensor ring 13. Through the U-shaped profile the rotor 1 has an upper ring 10*a* and a lower ring 10*b* which are connected to one another via the web. Whereas the upper ring 10*a* has a structure with projections 12*a* and recesses 11*a*, the lower ring 10*b* has no structure. A rotor of this kind is advantageous in so far as the vibratory forces which arise as a result of the structuring are reduced, since the lower ring 10*b* has no structure. In addition, it is possible to measure the position of the rotor with the help of Hall sensors in the air gap of the lower ring. Otherwise, the advantages correspond to those of the rotor in accordance with FIG. 19. In addition, the reluctance forces with respect to an axial journalling of the rotor are greater (due to the groove between the individual "rings" of the U-shaped profile).

Figure 21:
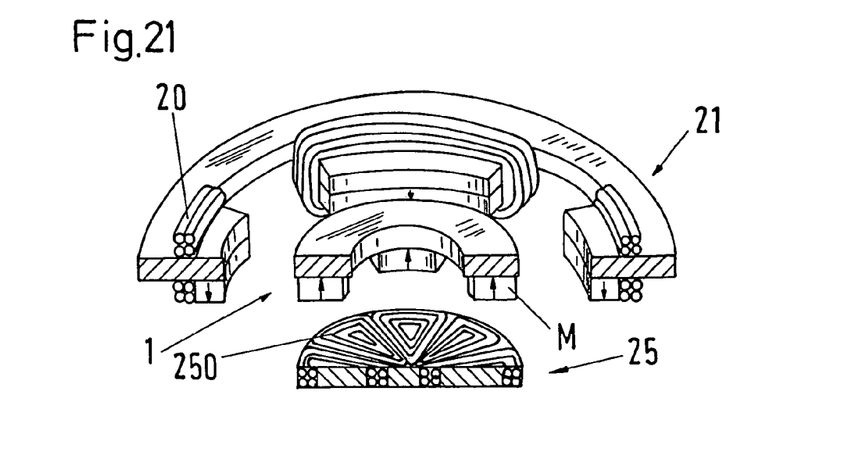
FIG. 21 shows an exemplary embodiment of the rotational arrangement in accordance with the invention in which the motor stator is provided with a disc rotor winding.

FIG. 21 shows an exemplary embodiment of the rotational arrangement in accordance with the invention with a bearing stator 21 of the already described kind with axially magnetized permanent magnets M arranged at one side and with a motor stator 25 with a disc rotor winding 250. A disc rotor winding is, so to speak, a flat winding which is arranged in a plane for the production of a rotary field. Disc rotor windings are known per se and can, in particular, have a multiple layer structure. The disc rotor winding is preferably without iron, through which axial drawing forces on the rotor 1 are practically completely avoided.

Figure 22:
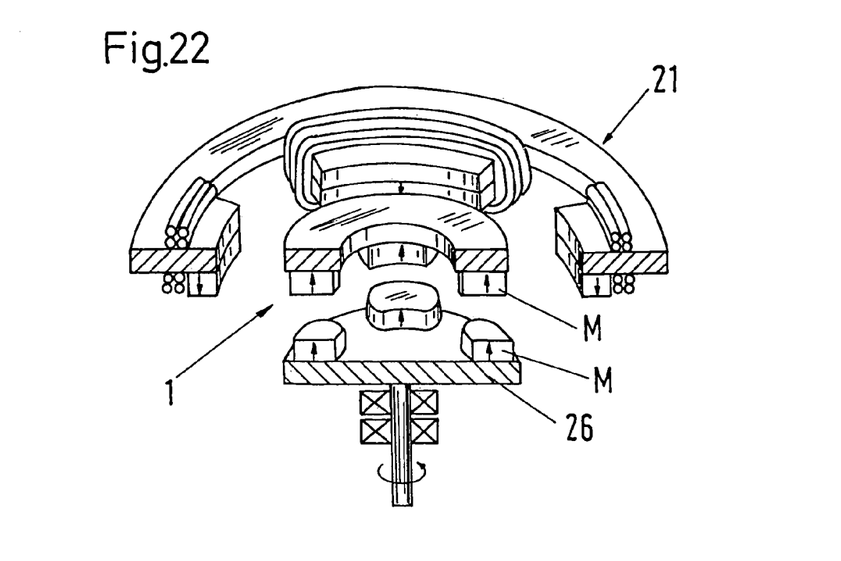
FIG. 22 shows an exemplary embodiment of the rotational arrangement in accordance with the invention in which the rotation of the rotor is produced by a drive which can be permanent magnetically coupled to the rotor.

FIG. 22 shows an exemplary embodiment of the rotational arrangement in accordance with the invention in which the rotation of the rotor 1 is produced with the help of a drive which can be permanent magnetically coupled to the rotor 1. The bearing stator 21 and the rotor 1 correspond here to the bearing stator 21 and the rotor 1 of FIG. 21. Only the drive is designed differently; here it comprises namely a disc 26 consisting of ferromagnetic material on which axially magnetized permanent magnets M are arranged, with the arrangement of the permanent magnets M on the disc 26 corresponding to the arrangement of the permanent magnets M on the rotor 1. The disc 26 is drivably mechanically journalled. When the disc 26 is driven, the rotor 1 synchronously follows the rotation of the disc 26 via the permanent magnetic coupling (here permanent magnetic axial coupling) as a result of the reluctance forces.

Figure 23:
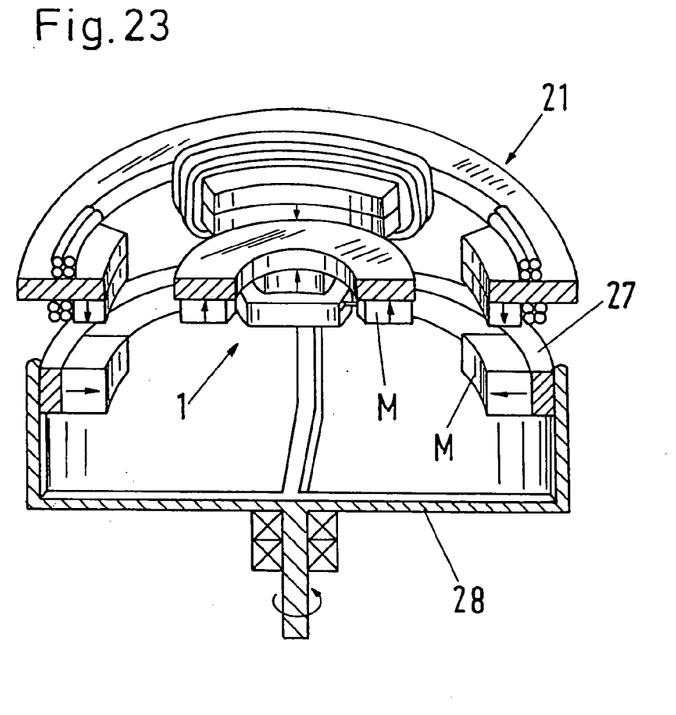
FIG. 23 shows an exemplary embodiment of the rotational arrangement in accordance with the invention analogous to FIG. 22 in which the permanent magnetic coupling of the drive is produced by means of radially magnetized permanent magnets.
Figure 24:
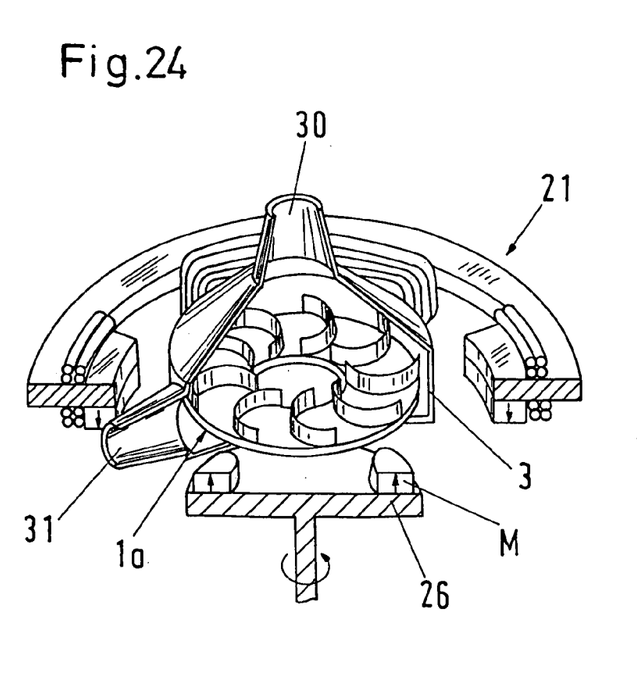
FIG. 24 shows a use of the rotational arrangement in accordance with the invention in the form of a pump, in particular, for highly pure or biological liquids, especially for blood.

The exemplary embodiment in accordance with the invention of FIG. 23 differs from the exemplary embodiment of FIG. 22 only in that the permanent magnets M of the drive are not mounted on a ferromagnetic disc but on a ferromagnetic ring 27 which in turn is connected to a connecting rod 28 which is drivably mechanically journalled. The operating principle is the same: As a result of the reluctance forces, the rotor 1 follows synchronously during a rotation of the connecting rod. Finally, FIG. 24 shows a use of the rotational arrangement in accordance with the invention in the form of a pump, in particular, for highly pure or biological liquids, especially blood. The bearing stator 21 and the drive 26 correspond here to the corresponding parts of the exemplary embodiment in accordance with FIG. 22. The rotor is designed here as a vaned wheel 1*a* and is arranged in a closed pump housing 3 of a magnetically poorly conducting material (e.g., plastic or chrome steel). The pump housing 3 has two connection pieces 30 and 31 for the intake and outlet of the liquid to be forwarded, for example, blood. A pump of this kind must be regularly disposed of after a single use. This can be done in a simple manner by pulling the intake and outlet lines off the connection pieces 30 and 31 and inserting a new pump housing. The remaining apparatus can be reused; moreover, the replacement of the pump housing can be carried out simply and comfortably.

Furthermore, it should be mentioned that in the rotational arrangement in accordance with the invention, in particular, with respect to its use as a blood pump, a number of aspects from WO-A-96/31934 are conceivable. Thus, both an inner rotor and an outer rotor are conceivable. Furthermore, as already mentioned, a hermetic partition (such as e.g., a gap tube or a vessel) can be arranged between the stator and the rotor. The rotor itself can be encapsulated with a plastic, with a ceramic or with another non-metallic material. Furthermore, as has already partially been described, a ring of electrically well conducting but magnetically poorly conducting material which is arranged around the rotor can be provided and can serve as a sensor ring for the position measurement by means of eddy currents. The determination of the respective angular position of the rotor can be done by means of Hall sensors, which can likewise serve as position sensors, which is advantageous in the measurement across an electrically conducting gap tube. The rotor together with the vessel surrounding it (see e.g., the blood pump described with reference to FIG. 24) can be replaceable and disposable or recyclable in order to be able to guarantee sterility. More details on all these topics can be found in WO-A-96/31934.

In particular, the sensor system, in uses in which a vessel is arranged between the stator and the rotor (e.g., the pump housing 3 in FIG. 24), shall again be discussed because the eddy current sensors which are typically used for the determination of the position of the rotor 1 relatively quickly reach their limits when certain materials (e.g., chrome steel) are used for the vessel (or for the pump housing, respectively). Here magnetic sensors, in particular, the above-mentioned Hall sensors, prove particularly advantageous. How Hall sensors of this kind can be arranged is shown in the exemplary embodiment of FIG. 25. The exemplary embodiment illustrated there corresponds to the exemplary embodiment of FIG. 14 (segment arrangement); here, the sensors are arranged and/or designed differently.

Figure 25:
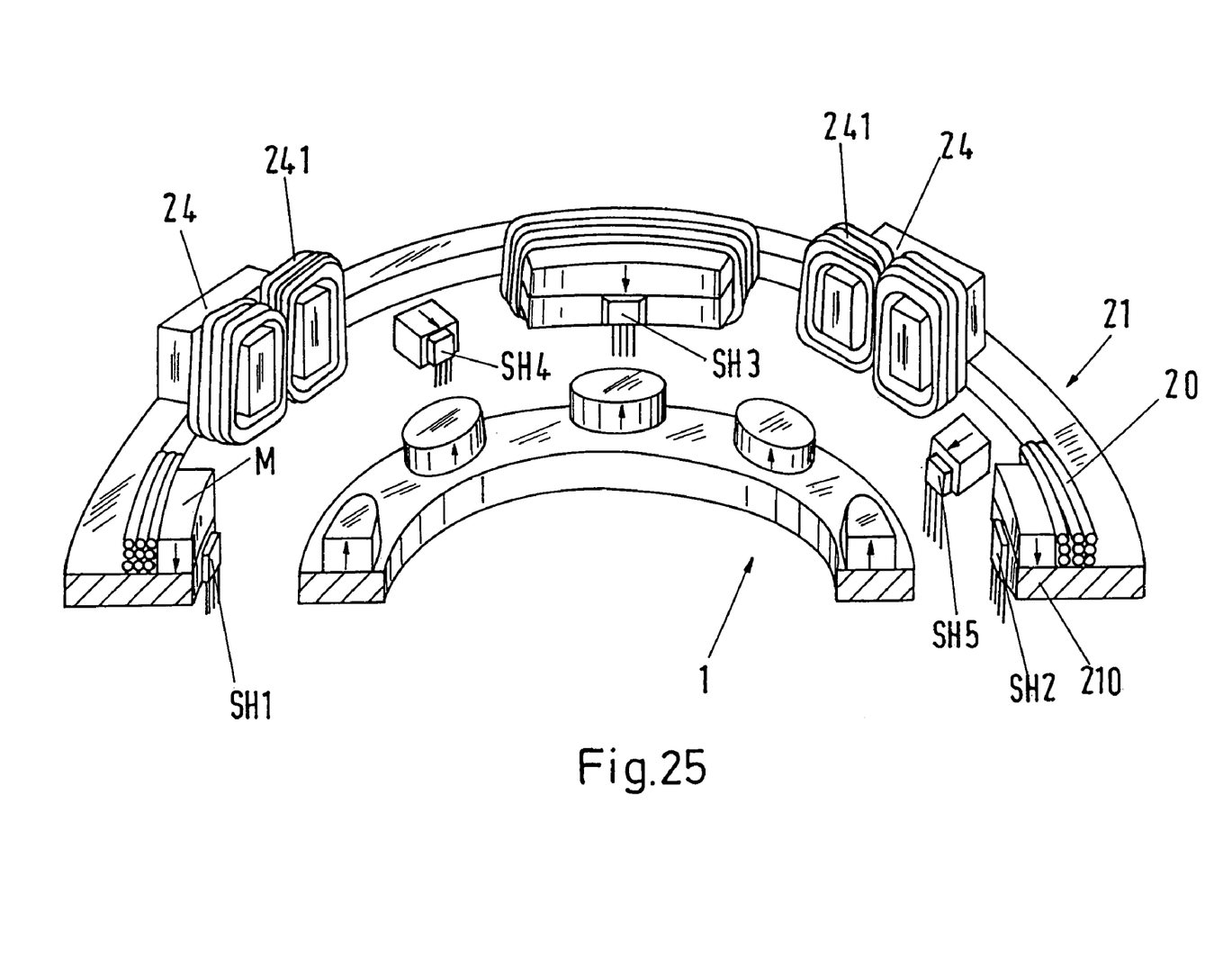
FIG. 25 shows the arrangement of FIG. 14 (segment arrangement) with a different sensor system.

In principle, the Hall sensors can be arranged in the air gap between the bearing stator 21 and the rotor 1. They can, in particular, also be mounted (e.g., adhesively fixed) on the teeth 210 of the bearing stator 21, as the Hall sensors SH1, SH2, SH3 are. In this case, the Hall sensors are arranged on a separate permanent magnet. In both variants, the Hall sensors are permeated by a relatively large rest flux (in the adhesively fixed variant this is produced by permanent magnets in the stator, in the other variant by the separate permanent magnet located directly at the sensor) so that the possible influence of stray fields, which are produced by the coil cores 24 and their windings 241, is slight. Without a rest flux, comparatively large fluctuations in the flux would otherwise arise through the permanent magnets moving past. For the determination of the position of the rotor in the respective direction, the difference of the signals from two geometrically oppositely disposed sensors is particularly suitable, even if one sensor per direction would theoretically be sufficient.

The invention claimed is:

1. A magnetically journalled rotational arrangement comprising a substantially disc-shaped or ring-shaped magnetically journalled rotor and
a stator comprising:
means for generating a field, wherein said field produces rotation of the rotor having means for generating a unipolar bias magnetic flux spatially modulated when viewed in the circumferential direction; and
a plurality of permanent magnets arranged to cooperate with the means provided on the rotor generating the spatially modulated bias magnetic flux and producing or reinforcing the magnetic journalling of the rotor,
wherein the stator effecting the magnetic journalling of the rotor surrounds the ring or disc-shaped rotor,
wherein the stator plane and the rotor plane coincide and from a bearing plane, and
wherein the means for generating the field are arranged in the segments between the permanent magnets in the stator so that the motor plane in which the rotation of the rotor is produced and the bearing plane in which the journalling of the rotor is produced coincide.

2. A rotational arrangement in accordance with claim 1 wherein the means for the production of the field which effects the rotation of the rotor and which is arranged in the segments between the permanent magnets has U-shaped coil cores with windings, with the U-shaped coil cores being arranged in the bearing plane.

3. A rotational arrangement in accordance with claim 1 wherein the means for the production of the field which effects the rotation of the rotor and which is arranged in the segments between the permanent magnets has U-shaped coil cores with windings, with the U-shaped coil cores being arranged perpendicular to the bearing plane.

4. A rotational arrangement in accordance with claim 1 wherein the permanent magnets are arranged at both sides of the disc-shaped or ring-shaped rotor.

5. A rotational arrangement in accordance with claim 1 wherein the permanent magnets have an axial or a radial magnetization.

6. A rotational arrangement in accordance with claim 1 wherein permanent magnets are provided both on the rotor and on the stator; and wherein both the permanent magnets provided on the rotor and the permanent magnets arranged on the stator are magnetized in the axial direction.

7. A rotational arrangement in accordance with claim 1 wherein permanent magnets are provided both on the rotor and on the stator; and wherein both the permanent magnets provided on the rotor and the permanent magnets arranged on the stator are magnetized in the radial direction.

8. A rotational arrangement in accordance with claim 1 wherein permanent magnets are provided both on the rotor and on the stator; and wherein the permanent magnets provided on the rotor are magnetized in the axial direction while the permanent magnet arranged on the stator are magnetized in the radial direction or vise versa.

9. A rotational arrangement in accordance with claim 1 wherein control windings are provided in the stator in order to control the spatially modulated unipolar bias magnetic flux.

10. A rotational arrangement in accordance with claim 1 wherein the stator producing the magnetic journalling of the rotor is designed to be substantially ring-shaped and surrounds the ring or disc-shaped rotor, with the stator plane and the rotor plane coinciding and forming the bearing plane; and wherein the stator comprises at least one further ring or disc-shaped motor stator which is arranged in a motor plane parallel to the bearing plane.

11. A magnetically journalled rotational arrangement comprising a substantially disc-shaped or ring-shaped magnetically journalled rotor and
a stator comprising:
means for generating a field, wherein said field produces rotation of the rotor having means for generating a unipolar bias magnetic flux spatially modulated when viewed in the circumferential direction; and
a plurality of permanent magnets arranged on both sides of the rotor to cooperate with the means provided on the rotor generating the spatially modulated bias magnetic flux and producing or reinforcing the magnetic journalling of the rotor, wherein the stator plane and the rotor plane coincide and from a bearing plane, and wherein the stator producing the magnetic journalling of the rotor surrounds the ring or disc-shaped rotor, and the stator further comprises two ring-shaped motor stators, wherein the first motor stator is arranged in a first motor plane parallel to the bearing plane on the one side of the bearing stator and the second motor stator in a second motor plane parallel to the bearing plane.

12. A magnetically journalled rotational arrangement comprising a substantially disc-shaped or ring-shaped magnetically journalled rotor and a stator comprising:

means for generating a field, wherein said field produces rotation of the rotor having means for generating a unipolar bias magnetic flux spatially modulated when viewed in the circumferential direction; and a plurality of permanent magnets arranged to cooperate with the means provided on the rotor generating the spatially modulated bias magnetic flux and producing or reinforcing the magnetic journalling of the rotor, wherein the stator plane and the rotor plane coincide and from a bearing plane, and wherein the stator producing the magnetic journalling of the rotor surrounds the ring or disc-shaped rotor, and the stator further comprises a disc-shaped motor having a disc rotor winding and arranged in a motor plane parallel to the bearing plane.

13. A rotational arrangement in accordance with claim 1 wherein the means for the production of the field which effects the rotation of the rotor comprises a rotatable drive which can be magnetically coupled to the rotor and the axis of rotation of which coincides with the axis of rotation of the rotor.

14. A rotational arrangement in accordance with claim 13 wherein the drive comprises permanent magnets which are magnetized in the axial direction.

15. A rotational arrangement in accordance with claim 13 wherein the drive comprises permanent magnets which are magnetized in the radial direction.

* * * * *